United States Patent
Möddel et al.

(10) Patent No.: US 9,248,112 B2
(45) Date of Patent: *Feb. 2, 2016

(54) HEMODIALYSIS AND PERITONEAL DIALYSIS SOLUTIONS COMPRISING ONE OR MORE CREATINE COMPOUNDS

(75) Inventors: Michael Möddel, Dallikon (CH); Theo Wallimann, Bergdietikon (CH)

(73) Assignee: CREARENE LTD., Nassau (BS)

( * ) Notice: Subject to any disclaimer, the term of this patent is extended or adjusted under 35 U.S.C. 154(b) by 184 days.

This patent is subject to a terminal disclaimer.

(21) Appl. No.: 13/263,189

(22) PCT Filed: Mar. 10, 2010

(86) PCT No.: PCT/CH2010/000065
§ 371 (c)(1),
(2), (4) Date: Dec. 12, 2011

(87) PCT Pub. No.: WO2010/115291
PCT Pub. Date: Oct. 14, 2010

(65) Prior Publication Data
US 2012/0101069 A1   Apr. 26, 2012

(30) Foreign Application Priority Data
Apr. 6, 2009 (EP) .................................. 09005038

(51) Int. Cl.
| | |
|---|---|
| *A01N 57/00* | (2006.01) |
| *A61K 31/66* | (2006.01) |
| *A01N 37/44* | (2006.01) |
| *A61K 31/195* | (2006.01) |
| *A61K 31/198* | (2006.01) |
| *A61K 9/00* | (2006.01) |
| *A61K 9/08* | (2006.01) |
| *A61K 47/02* | (2006.01) |
| *A61K 47/26* | (2006.01) |

(52) U.S. Cl.
CPC ............ *A61K 31/198* (2013.01); *A61K 9/0019* (2013.01); *A61K 9/08* (2013.01); *A61K 47/02* (2013.01); *A61K 47/26* (2013.01)

(58) Field of Classification Search
USPC ................................. 514/115, 565
See application file for complete search history.

(56) References Cited

U.S. PATENT DOCUMENTS

| | | | |
|---|---|---|---|
| 7,235,382 B2* | 6/2007 | Endo et al. ................... | 435/69.1 |
| 2003/0013767 A1* | 1/2003 | Bessman ....................... | 514/565 |
| 2009/0005450 A1 | 1/2009 | Nivaggioli | |

FOREIGN PATENT DOCUMENTS

| | | |
|---|---|---|
| EP | 0 854 712 B1 | 5/2003 |
| WO | 01/00203 A1 | 1/2001 |
| WO | 01/00212 A1 | 1/2001 |
| WO | 03/101402 A2 | 12/2003 |
| WO | 2008/052712 A1 | 5/2008 |
| WO | 2008/073332 A2 | 6/2008 |
| WO | 2009/002913 A1 | 12/2008 |

OTHER PUBLICATIONS

Sam et. al. (Hemodialysis International (2006) 10:15-28).*
Tokarska-Schlattner M, Epand RF, Meiler F, Zandomeneghi G, Neumann D, et al. (2012) Phosphocreatine Interacts with Phospholipids, Affects Membrane Properties and Exerts Membrane-Protective Effects. PLoS ONE 7(8): e43178. doi:10.1371/journal.pone.0043178; Aug. 17, 2012; http://www.plosone.org/article/info%3Adoi%2F10.1371%2Fjournal.pone.0043178.
Chang Chiz-Tzung et al: "Creatine monohydrate treatment alleviates muscle cramps associated with haemodialysis"; Nephrology Dialysis Transplantation, Oxford University Press, GB; vol. 17, No. 11; Nov. 1, 2002; pp. 1978-1981; XP002546996.

* cited by examiner

*Primary Examiner* — Marcos Sznaidman
(74) *Attorney, Agent, or Firm* — Rankin, Hill & Clark LLP

(57) ABSTRACT

The present invention relates to a haemodialysis solution or concentrate thereof comprising creatine compound(s) and the use of creatine compound(s) for preparing a dialysis solution or concentrate thereof. Furthermore, the present invention is directed to a method for preparing creatine-containing dialysis solutions and concentrates. In addition, the present invention is directed to a method for treating patients with dialysis dependent renal failure with creatine compounds and to provide a variety of significant health benefits and improvement of life quality parameters for dialysis patients. This is achieve by supporting and improving the physiological functions of the patients organs and cells via creatine compounds delivery to the patients, and by protecting organs and cells (specifically including blood cells) of these patients from deleterious effects of a variety of endogenous or exogenous cellular stressors that are linked to the disease state or to the clinical treatment modalities. Furthermore in peritoneal dialysis solutions creatine can be used as an osmotic agent preventing side effects caused by high glucose supplementation.

13 Claims, No Drawings

HEMODIALYSIS AND PERITONEAL DIALYSIS SOLUTIONS COMPRISING ONE OR MORE CREATINE COMPOUNDS

The present invention relates to a hemodialysis solution and peritoneal dialysis solution or concentrates thereof and to the use of creatine compound(s) for preparing a dialysis solution or concentrate thereof Furthermore, the present invention is directed to a method for preparing creatine-containing hemodialysis and peritoneal dialysis solutions and concentrates. In addition, the present invention is directed to a method for treating patients with renal failure, who depend on dialysis treatment, to enhance their creatine levels in cells and organs and improve their health status.

Finally, the present invention is directed to a method for treating peritoneal dialysis patients with high concentrations of creatine compounds as active osmolytes, alone or in combination with other osmotically active substances, in order to significantly reduce the high glucose concentrations in peritoneal dialysis fluid that eventually lead to fibrosis of the peritoneum and an induction of diabetes-II.

BACKGROUND OF THE INVENTION

The present invention is directed to the field of creatine supplementation and hemodialysis and/or peritoneal dialysis for patients with renal failure, who depend on dialysis treatment. Creatine is a natural body substance involved In numerous physiological functions and, hence, of particular relevance for the vertebrate organism, in particular the brain, skeletal and cardiac muscle, where most of the creatine is located in adult mammals (120 to 150 g for a human of about 75 kg weight). Creatine and phosphocreatine are the key substrates of the creatine/phosphocreatine-kinase system that supplies cells with energy. In cells creatine kinase reversibly converts phosphocreatine (PCr) and ADP into ATP and creatine. This reversible reaction plays a key role in the energy metabolism of skeletal and cardiac muscle, the brain, sensory cells, e.g. retina and inner ear, as well as sperm and other cells. The creatine/phoshocreatine-kinase system has a dual function. It represents an immediately available, high energy phosphate buffer system for regenerating ATP as well as an intracellular energy transport system or shuttle between either mitochondria or sites of glycolysis to those places where energy is needed, e.g. at sites of high ATPase activity (for cell locomotion, ion-pumping etc). More specifically, the creatine system sustains the local cellular ADP/ATP-ratio in the vicinity of ATPases and thereby ensures the effective functioning of these ATPases. The concentration of phosphocreatine/creatine is much higher than that of ADP/ATP, has a lesser influence on cell metabolic regulation and replenishes ATP upon demand. Furthermore, ATP and ADP have limited diffusion abilities whereas creatine and phospho-creatine are readily diffusing from either mitochondria or from regions of ATP production by glycolysis to those places where energy and ATP is needed. Nutritional or supplemented Creatine is actively transported into cells by a Creatine-Na/K-cotransporter (CrT).

In animal experiments it was demonstrated that creatine deficit leads to functional abnormalities and histopathological changes in muscle similar to those of patients with mitochondrial myopathies. Creatine kinase knock-out mice (in brain and muscle) demonstrated a significant loss of muscle power and problems relating to muscle relaxation, due to creatine's key role in providing the contractile apparatus and the calcium ion pumps with energy. Also, these transgenic mice show irregular behavioral phenotypes and histological abnormalities in muscle and brain. Patients with genetic deficits in the creatine metabolism present with severe neurological symptoms. For example, children with these genetic defects show development disorders, speech delay, autism and epilepsy. Depending on the type of genetic defect oral creatine supplementation can reverse these abnormalities.

Creatine supplementation has been shown to elicit significant cell protective, antioxidant and even anti-apoptotic effects, in particular for skeletal and cardiac muscle cells, as well as for nerve and skin cells. These effects of creatine are of benefit for healthy people as well as patients with diverse muscular, neuromuscular, neurological and neurodegenerative disorders. Endogenous creatine is mainly produced in the kidney and liver. Specifically, in the kidney guanidino-acetate is produced from arginine and glycine and subsequently methylated by activated methionine to methyl guanidino acetate, i.e. creatine, in the liver. The daily human demand for creatine is approximately 3 to 4 g, whereas the endogenous production is limited to about 1 to 2 g/day. Natural creatine is mainly available in fish and meat and to some extent also in milk.

Dietary Creatine, taken up with meat and fish consumption, or supplementation of Creatine in form of chemically pure substance (e.g. Creatine Monohydrate or Creatine salts) has a number of benefits and advantages for humans. Naturally, it helps for compensating the chronic creatine deficits of vegetarians. Also, it is an officially authorized diet supplement for athletes leading to an enhanced cellular energy status that results in prolonged muscle endurance, in a delay of muscle fatigue and in an accelerates muscle recuperation. Moreover, creatine supplementation has shown to be beneficial in a number of muscular, neuromuscular, neurological and neurodegenerative diseases, for example, congestive heart failure, cardiac insufficiency, cardiac arrhythmia, muscle disuse atrophy, gyrate atrophy, McArdle's disease, diabetic and toxic neuropathies, peripheral nervous system diseases, dysmyelination and demyelination diseases, motor neuron disease, traumatic nerve injury, multiple sclerosis, mitochondrial diseases, muscular dystrophy, amyotrophic lateral dystrophy (ALS), Morbus Huntington, Morbus Parkinson, Charcot Marie tooth syndrome, epilepsy, stroke, spine injuries, cranial cerebral injury, brain atrophy, cognitive dysfunction (see EO 03/101402 A2) osteoporosis, skin disorders (see WO 2008/073332, WO 01/00203 A1), dermatitis (see W02009/002913), eye disorders (see US 2009/0005450 A1), transmissible spongiform encephalopathies (see WO 01/00212), disorders of the glucose metabolism (see EP 0 854 712 B1).

The positive effects of creatine supplementation are directly or indirectly based on its effect on the energy status of cells, its ability to protect cells and its anti-apoptotic influence.

Clinical studies have demonstrated creatine to be safe up to extremely high doses, for example up to 20 g daily intake for adults. Up to date no serious side effects are known. Creatine in the form of creatine monohydrate is a white powder that can be stored at room temperature. In acidic aqueous solutions it displays some instability at temperatures over 60° C. At neutral pH and cooled, however, it can be stored for thirty days without losses. When administered orally, most of the creatine passes unchanged through the acidic stomach environment. Next to creatine monohydrate, which is only moderately soluble in water, a number of more soluble salts like creatine pyruvate and citrate are commercially available. For people with severely reduced body creatine levels, an initial loading phase with 4×5 g of creatine per day during a 7-10 days period, followed by a low dose daily intake of 3 to 6 g is generally recommended. It has been shown that the simultaneous administration of creatine and glucose is beneficial in order to compensate for energy losses due to creatine phosphorylation.

Hemodialysis is used for providing an artificial replacement for lost kidney function due to renal failure. Dialysis may be used for patients with sudden but temporary loss of kidney function (acute renal failure) or for patients permanently lacking kidney function (stage 5 chronic kidney disease). When healthy, the kidneys maintain the body's internal equilibrium of water and minerals and remove the daily metabolic load of waste products and toxins from the blood. As part of the endocrine system they produce erythropoletin and 1.25-dihydroxycholecalciferol (calcitriol). Dialysis is an imperfect treatment for replacing kidney function because it does not correct the endocrine functions of the kidney. It replaces the excretory function through diffusion (waste removal) and ultrafiltration (fluid removal) of solutes. But prolonged dialysis treatment also leads to a wash-out of valuable body substances (minerals, vitamins and other nutrient compounds, which are lost during the dialysis process, due to lack of resorption by the kidneys. Therefore, dialysis patients are creatine-depleted because endogenous creatine synthesis is hampered in the diseased kidney and ingested creatine is washed out during dialysis.

Hemodialysis works on the principles of (i) diffusion of solutes and (ii) ultrafiltration of fluid across a semi-permeable membrane. On one side of the semi-permeable membrane blood flows by and the dialysate flows by the opposite side. Small and medium-size solutes (typically up to 25 kDa) and fluid pass through the membrane. The counter-current flow of blood and dialysate maximizes the concentration gradient of solutes between the blood and dialysate, which helps to remove more urea and creatinine from the blood. The concentrations of solutes (for example potassium, phosphorus, and urea) are undesirably high in the blood, but low or absent in the dialysis solution and constant replacement of the dialysate ensures that the concentration of undesired solutes is kept low on this side of the membrane. The dialysis solution has levels of minerals similar to their natural concentration in healthy blood. For another solute, bicarbonate, dialysis solution level is regularly set at a slightly higher level than in normal blood, to encourage diffusion of bicarbonate into the blood, to act as a pH buffer to neutralize the metabolic acidosis that is often experienced in these patients. The levels of the dialysate components are typically prescribed by a nephrologist according to the needs of the individual patient.

In hemodialysis, the patient's blood is pumped through the blood compartment of a dialyzer exposing it through a semipermeable membrane to the compartment of the dialysis solution and Diffusion of salutes is possible. The cleansed blood is then returned via the circuit back to the body. Ultrafiltration occurs by increasing the hydrostatic pressure across the dialyzer membrane. This is usually done by applying a negative pressure to the dialysate compartment of the dialyzer. This pressure gradient causes water and dissolved solutes to move from blood to dialysate and allows the removal of several litres of excess fluid during a typical three to five hour treatment.

In peritoneal dialysis a sterile solution containing minerals and glucose is run through a tube into the peritoneal cavity, the abdominal body cavity encasing the intestines, where the peritoneal membrane acts as a semipermeable membrane. The dialysate is left there for a period of time to absorb waste products and then it is drained out through the tube and discarded. This cycle or "exchange" is normally repeated four to five times a day (CAPD: Continuous Ambulatory Peritoneal Dialysis), and sometimes overnight with an automated system (APD: Automated Peritoneal Dialysis). Ultrafiltration occurs via osmosis; the dialysis solution used contains a high concentration of glucose, and the resulting osmotic pressure causes fluid to move from the blood into the dialysate. The amount of ultrafiltration is directly dependent from the level of concentration of glucose or other osmotic active substances such as poly-sugars (eicodextrin) or amino acids. As a result, more fluid is drained than was instilled.

Hemofiltration is a treatment similar to hemodialysis, but it makes use of a different principle. The blood is pumped through a dialyzer or "hemofliter" as in dialysis, but no dialysate is used. A pressure gradient is applied; as a result water moves across the very permeable membrane rapidly, "dragging" along with it many dissolved substances, importantly ones with large molecular weights, which are cleared less well by hemodialysis. Salts and water lost from the blood during this process are replaced with a "substitution fluid" that is infused into the extracorporeal circuit during the treatment. Hemodiafiltration is a term used to describe several methods of combining hemodialysis and hemofiltration in one process.

Due to the loss of excretory function the blood volume and the metabolic toxic load that accumulates between dialysis treatments regularly reaches an unhealthy range leading to an increased number of disorders directly related to renal failure and dialysis treatment, e.g. hypotension, hypertension, muscle cramps, fatigue, nausea, vomiting. Furthermore, the high mechanical (shearing forces) and immunological stress (bioincompatibility of contact surfaces) regularly imposed on the blood and the blood cells in the dialyzer leads to further and often chronic disorders, e.g. hemolysis, amyloidosis, probably malnutrition and cardiovascular morbidity and mortality. Loss of physiologically functioning blood cells, e.g. erythrocytes and immune cells due to mechanical and chemical stress during dialysis treatment is a major problem for patients undergoing regular long-term dialysis treatment. The choice of materials for the dialyzer and an accompanying anticoagulant treatment, including the choice of optimally composed blocompatible dialysis fluids is often an important factor influencing patient mortality.

Cell and Organ Protection by Creatine
Modes of Action and Pleiotropic Functions of Creatine Compounds for Cell and Organ Protection
Anti-catabolic Effects of Creatine It has been found out that creatine generally enhances muscle cell proliferation and muscle cell differentiation. For example, creatine has been shown to enhance the release of growth hormone (GH), insulin-like growth factors (IGF-I and IGF-1), as well as insulin itself. In addition, creatine promotes the expression of myogenic transcription factors and positively affects muscle cell signaling via the Akt/PKB signaling pathway. Finally, creatine promotes the recruitment and division of muscle satellite cells that are important for muscle build-up and repair. Since endogenous synthesis of creatine uses a significant proportion of the cells activated methionine in the form of S-adenosyl-methionine (SAM), external creatine supplementation spares labile methyl groups in the form of SAMS which then is available for protein synthesis, cell and tissue anabolism.

All these effects contribute to the anti-catabolic effects of creatine and lead to an improvement and/or maintenance of muscle cells and lean body mass, as well as muscle strength and better coordination of movement. This holds especially true in situations of muscle-disuse by which muscle atrophy is induced. Immobilization and muscle cell loss is indeed a general problem in dialysis patients. creatine has been shown to prevent such immobilization-induced muscle cell atrophy and to improve and speed-up rehabilitation. Therefore, by preventing catabolic events and loss of cells, creatine supplementation also helps dialysis patients to be able to maintain their muscle cell mass and to keep their physiological functions, which positively affects life quality and mobility, resulting In more independence and security for the patient. By doing so creatine supplementation with creatine compounds delays entrance into the disability zone, thus extending a plethora of positive life-quality parameters for such dialysis patients.

Improvement of Cellular Energy Status of Cells and Organs.

As a consequence of creatine supplementation, cells take up creatine that Is subsequently phosphorylated by intra-cellular creatine kinase to give high-energy-rich Phospho-Creatine (PCr). By elevation of intra-cellular Phospho-Creatine levels, creatine supplementation improves the cellular energy status, i.e. by increasing the PCr/ATP energy-charge ratio and intracellular energy trafficking via the PCr/Cr shuttle (Wallimann et al. 2007). Creatine stimulates mitochondrial respiration and thus improves energy production in mitochondria. Creatine also activates the AMP-stimulated protein kinase (AMPK) a general energy sensor and cell stress kinase that improves energy provision via enhancing glucose uptake and oxidation in cells. Such energy charging of cells by Creatine compounds leads to higher metabolic activity of cells and improved cell function.

Prevention of Mitochondrial Permeability Pore Opening, Membrane Damage and Cell Death (Apoptosis)

Creatine prevents mitochondrial swelling and induction of programmed cell death (apoptosis), thus rendering cells more resistant to metabolic and environmental stress. Creatine and even more so, Phospho-Creatine, as amphiphiles, are able by interaction with lipid bilayers to stabilize membranes and cells against mechanical and osmotic stress. Since these cells are able to take up external Creatine and express creatine kinase, some of the supplemented Creatine taken up is then converted into Phospho-Creatine, which can invoke membrane stabilization and protection from the intro-cellular side of the cell. These latter facts are especially relevant for protection by Creatine, Phospho-Creatine or other Creatine compounds of erythrocytes and of white blood cells during the dialysis process, when both metabolic and mechanical stress is imposed on these very cells during the dialysis process. Thus supplementation of dialysis fluid by a Creatine compound leads to significant cell protection and thus to a health benefit for dialysis patients.

Direct and Indirect Anti-oxidant Effects of Creatine, Reduction of Advanced Glycosylation End Products (AGE) And Anti-aging of Cells and Organs Creatine has been shown to act either directly or indirectly as an anti-oxidant to cells in vitro and in vivo and thus exert protective effects on cells and tissues against oxidative stress and lipid peroxidation, including lowering of TBARS (thiobarbituric-acid reaction products); 2008). Thus, Creatine generally protects cells in the body from numerous stress factors. This protection is especially relevant again for dialysis patients whose erythrocytes and white blood cells are mechanically and oxidatively stressed during the process of dialysis. Therefore, Creatine compounds reduce anemia and weakening of the immune response that are commonly observed in dialysis patients. Creatine enhances the levels of camosin and anserin in muscle, compounds that are involved in reducing Advanced Protein Glycation (AGE) that is inflicted in faster cell aging. Thus, supplementation by Creatine compounds leads to cell protection and acts as anti-aging intervention also for dialysis patients.

Reduction of Homocysteine Levels by Creatine Supplementation

Creatine supplementation has been shown to reduce serum levels of homocystelne, in an animal model, a significant cardiovascular risk factor that is also generally elevated in haemodialysis patients. Another study showed a reduction of homocystein levels upon creatine supplementation in humans with approximately 5 g Cr/day. With a lower daily dosage of 2 g/day, in additionally vitamin B supplemented subjects, no such effects were seen. It Is likely, however, that dialysis patients take profit from supplementation of a Creatine compound at a dosage of 5 g or more per day, with or without additional supplementation by Vitamin B complex, by reducing homocysteine concentration in their blood and thus lower the risk of cardiovascular and endothelial damage, which is a serious problem in dialysis patients.

Addition of Osmotically Active Creatine Makes Possible to Reduce Glucose Concentration in Peritoneal Fluid.

Creatine is an osmotically active substance and thus the glucose concentration needed to obtain the osmolarity needed for peritoneal dialysis fluids can be reduced significantly, thus alleviating the bio-incompatibility of chronic high-glucose exposure of the peritoneum that eventually may lead to fibrosis of the peritoneum and Diabetes II with all its negative consequences for health.

Other Actions of Creatine On Cells and Organs.

It is obvious to the educated reader that Creatine acts as a pleiotropic nutritional supplement. Therefore, it is likely that there are many more positive effects of Creatine on cells and tissues that have not been described yet and that are still waiting to be discovered. It is thus self-understood that dialysis patients would eventually profit from those effects, as well. For a detailed review on creatine and its physiological impact on healthy and diseased humans see the article of Theo Wallimann, "Kreatin-warum, warm und für wen?", Schweizer Zeitschrift für Ernährungsmedizin, 5/08, p. 29-40, 2008, which is incorporated herewith by reference.

Cell Protection by Creatine Compounds Relevant for Dialysis Patients

Protection of Residual Kidney Cell Function by Creatine Compounds

Haemodialysis patients often still show some residual renal function and in this case creatine, due to its cell protective and anti-apoptotic effects, can protect renal cells and stop or delay further degeneration and cell death in the kidney.

Protection of Blood Cells: Erythrocytes and Immune Cells by Creatine Compounds:

During the dialysis process, blood cells are subjected to metabolic, mechanical, osmotic and oxidative and other stresses, which can lead to toss of cell function and cell death. Thus, in dialysis patients, creatine will energetically charge blood cells, protect the cell against metabolic and oxidative stress and protect its membranes against mechanical stress, thus counteracting the loss of red blood cells, and together with erythropoietin (EPO) act synergistically to prevent anemia, a problem commonly encountered in haemodialysis patients. Since EPO, however, is known to cause serious side effects, by the addition of Creatine, which protects erythrocytes from haemolysis, less EPO is needed for treating haemodialysis patients and thus the probability of EPO-related side effects is lowered in haemodialysis patients by Creatine supplementation.

In addition, white blood cells, that is, cells of the immune system will also be protected by creatine and Phospho-Creatine from energy loss due to creatine depletion and by stabilizing cell membranes will protect these cells against mechanical stress. Thus, Creatine will maintain proper cell function and strengthen the patient's immune system, which is of paramount importance also for haemodialysis patients.

Protection of Muscle and Muscle Cells by Creatine Compounds

Due to its anti-catabolic effects (by increased of secretion of growth hormone and muscle differentiation factors), supplementation by Creatine compounds improves muscle cell mass, muscle cell function, proliferation and differentiation and finally overall muscle cell performance (force generation), parameters that are all highly relevant quality of life parameters for haemodialysis patients, who generally loose body weight, muscle mass and muscle force.

Protection and Maintenance by Creatine Compounds of Brain and Brain Cells from Uremic Toxins The neuro-protective effects of Creatine compounds are well documented (for review see Andres et al. 2008) and it is obvious that dialysis patients are also taking advantage from brain and nerve cell protection by creatine, resulting in tower fatigue levels, improved memory and learning function and general well-being.

In addition, uremic toxins are known to negatively influence brain function and morphology, and Creatine compounds are neuro-protective to a significant extent towards these toxins, some of them have been demonstrated to affect Creatine synthesis and Creatine transport in the brain, Creatine supplementation is exerting its neuroprotective effect towards such toxins and thus also improving brain function and life quality of dialysis patients.

Protection and maintenance of bone cells by Creatine compounds

Creatine enhances bone cell proliferation, differentiation and mineralization thus counteracting osteoporosis, osteomalacia and adynamic bone disease, problems often encountered in dialysis patients.

Anti-aging effects by Creatine Compounds on Cells and Organs

Supplementation by creatine compounds leads to protection of body cells and tissues, against oxidative stress, lipid peroxidation, advanced glycation end products (AGE's). These protective mechanisms of Creatine are true also and important for dialysis patients as well.

Creatine an Essential Supplement for Dialysis Patients

Dialysis Patients are generally catabolic and energy-depleted, as well as creatine-depleted in their skeletal muscles and in heart and other tissues and cells. The latter is due to a reduced endogenous synthesis in the kidney of guanidino acetate, the precursor of Creatine, as well as lower alimentary intake of Creatine by Dialysis patients compared to healthy meat-eaters. Creatine in this case turns out to be an essential nutrient for dialysis patients and externally added Creatine is absolutely necessary for normal physiological body and organ function in these patients.

Instead of forcing dialysis patients to consume 5-20 grams of Creatine powder daily by oral intake, Creatine is added directly to dialysis fluid from where it is taken up (unnoticed by the patient) into the blood and from there via the Creatine-Transporter into the target organs, such as muscle, brain and nervous tissue etc. By adding Creatine to the dialysis fluid only so much Creatine is taken up by the cells as is necessary to fill up the cellular Creatine pools and the rest of the Creatine remains in the dialysis fluid. The advantage of such treatment is that these patients are not burdened by an over-load of Creatine, which may be the case, if Creatine would be taken orally. Under the latter circumstances, excess of orally taken Creatine has to be eliminated and may represent a burden for the patients organism. If, however, Creatine is supplemented into the dialysis fluid, each patient, depending on his Creatine status, is taking up only as much Creatine as is needed to fill his cellular Creatine pools, and no elimination of creatine is necessary and no extra burden is inflicted on the patients system.

Addition of Osmotically Active Creatine Allows for Significant Reduction of the Glucose Concentration in Peritoneal Dialysis Fluid.

For peritoneal dialysis, the very high concentration of glucose or other osmolytes that potentially have negative effects, e.g. exposure to constantly high glucose concentration present the peritoneal fluid significantly increases in the dialysis patients the formation of Advanced Glycation Endproducts (AGE's), loss of transport function of the peritoneum and finally enhances the chances of weight increase and of acquiring Diabetes-II. Since Creatine is an osmotically active substance, the glucose concentration in the dialysis fluid can be significantly lowered if Creatine is added instead, in this case preferentially at the highest concentration possible, e.g. up to 24-25 g of Creatine per liter of dialysis fluid at a body temperature of 37° C. By this invention, deleterious side effects caused by high glucose exposure of the dialysis patient to this very fluid can be reduced. As an example Creatine concentrations near the respective solubility limit at the requested temperatures are added for this purpose to significantly reduce the glucose concentration but retain the require osmolarity for peritoneal dialysis. During a typical peritoneal dialysis set-up, the peritoneal dialysis fluid of 2-3 liters is replaced 4-5 times, that is, between 8-15 liters of peritoneal fluid are used per patient and treatment, such that the patient's peritoneum is exposed to a total of 8×25 to 15×25 g less of glucose, corresponding to 200 g to 375 g less glucose than with the regular peritoneal dialysis treatment. This reduction of glucose is highly significant.

Creatine may also be combined with other osmotically active compounds such as betaine, amino acids, mono- or poly-sugars of glucose or other sugar compounds, such that glucose can be even more reduced.

This strategy has two advantages in one, first creatine is used as osmolyte to substitute glucose and second, at the same time the creatine needed is transported through the peritoneum and taken up by the target organs of the patient. This combination is novel and it makes possible that chronic ambulatory peritoneal dialysis (CAPD) or automated peritoneal dialysis (APD), as a simpler and cheaper option of dialysis treatment as compared to hemodialyis, may be used for a much more prolonged period of time for the treatment of chronic renal failure patients, compared to conventional treatments.

Routes of Creatine Supplementation for Dialysis Patients

The routes of creatine delivery vary according to the specific needs of patients and modalities of the clinical setting. Creatine may be delivered via an oral, intra-peritoneal, intra-venous route or by the hemodialysis fluid.

1) For Oral Creatine Supplementation

The specific range of oral Creatine supplementation for dialysis patients would similar as used by athletes. The recommended range of daily Creatine intake would be at a dosage of 1-20 g Creatine per day (as Cr-monohydrate or other Cr-containing compounds, Cr-salts or Cr-analogs) taken orally in form of a powder, tablets, and aqueous solution or as a suspension. The preferred supplementation scheme would allow for 5-20 g of Creatine or Creatine analogs per day for a loading phase period of 7-14 days, followed by a maintenance phase of 2-5 g of Creatine per day during an unlimited time frame or as long as needed. Oral supplementation may also be combined with supplementation of creatine via dialysis fluid.

2) For Peritoneal And/Or Haemodialysis a) Addition of Creatine Directly to the Final Dialysis Fluid for Peritoneal or Hemodlalysis The novelty of the present invention and its preferred embodiment consists of the addition of Creatine (Mr 131.13 Daltons), Creatine-Monohydrate, Creatine-containing salts or Cr-analogs directly to the final dialysis solution. The specific, therapeutically effective range of Creatine concentrations for this application is from 0.05 m/l to 20 m/l final concentration of Creatine as Cr-monohydrate or other Cr-containing compounds Cr-salts or Cr-analogs added in its solid form (powder) to the final dialysis fluid, immediately before usage, to avoid the generation of unwanted creatinine during prolonged storage of Creatine in solution.

Creatine or Creatine-analogues are preferably to be added in solid state (as powder) immediately before the final dialysis solutions are made up. This has the advantage that Creatine, which is not very stable in solution at room temperature during, longer periods of time (weeks), is not converted to unwanted creatinine that otherwise would be generated by a spontaneous non-enzymatic chemical reaction during prolonged storage of Creatine in solution.

b) Addition of Creatine to the Dialysis Fluid Concentrate for Peritoneal or Hemodialysis The novelty of the present invention and its preferred embodiment consists of the addition of Creatine (Mr 131.13 Dattons) Creatine-Monohydrate, Creatine-containing salts or Cr-analogs to the concentrated dialysis stock solution (concentrate). For peritoneal dialysis this Creatine-containing concentrate is directly diluted before usage. For haemodialysis, creatine present in the concentrate would be continuously diluted during the course of haemodialysis, such that the patient is constantly exposed to an entirely physiological concentration of Creatine during the entire dialysis treatment process. This concentration of Creatine (in the final dialysis liquid) is in the range of 0.05 to 20 mM and thus in the same range as reached in the serum of subjects supplemented with a singly portion of 5-20 g of Creatine. The Creatine concentration proposed herein together with Creatine uptake during a 3-4 hr dialysis is sufficient to provide those cell protection effects and health benefits for the patient that are claimed here.

Creatine or Creatine-analogues are preferably added in solid state (as powder) immediately before the dialysis concentrate solutions are made up. This has the advantage that Creatine, which is not very stable in solution at room temperature during longer periods of time (weeks), is not converted to unwanted creatinine that otherwise would be generated by a spontaneous non-enzymatic chemical reaction during prolonged storage of creatine in solution.

3) For Peritoneal Dialysis: Creatine Compounds as Osmolytes for Peritoneal Dialysis The novelty of the present invention is that for peritoneal dialysis fluid, high concentrations of osmotically active Creatine or Creatine compounds are added to substitute or replace glucose or other osmolytes necessary for peritoneal dialysis.

By addition of high concentrations of osmotically active creatine in a peritoneal dialysis setting, 24-25 g of creatine, creatine salts, or creatine analogues per liter are added immediately to the final peritoneal dialysis solution at a temperature 37° C. These concentrations are near the saturation limit of creatine the solubility of which is highly sensitive to temperature. By this way, a maximum of osmotically active creatine compound can be dissolved and thus the glucose content in the peritoneal dialysis fluid can be reduced accordingly. In this set-up creatine compounds primarily act as osmolyte and only secondarily are taken up in a very small proportion of the total creatine compound added. Such a strategy, by significantly reducing glucose in the dialysis fluid, allows in the long-term to alleviate the potentially deleterious side effects of chronic exposure of the peritoneum and the dialysis patient to a high glucose load, e.g. fibrosis of the peritoneum and loss of function of peritoneal membranes and induction of diabetes in the patients.

For peritoneal dialysis, a high concentration of creatine is proposed herein, e.g. 24-25 g of creatine compound per liter of dialysis fluid 37° C. (up to approximately 190 mM/l) where creatine acts in the first place as an osmolyte to replace or reduce the high-glucose concentration. The crucial difference of peritoneal dialysis versus hemodialysis is that in the first case, the dialysis fluid is not in direct contact with the patient's blood system, since the peritoneal dialysis fluid is separated from the patients blood system by the peritoneum representing a biologically active filter equipped with transport systems and ion pumps. Whereas in hemodialysis the dialysis fluid is only separated by a metabolically inert and passive diffusion membrane. Therefore, for peritoneal dialysis, in contrast to hemodialysis where this should be avoided, creatine compounds can be added to the peritoneal dialysis liquid at high concentrations near saturation at body temperature. The uptake of creatine compound by the peritoneum then is a secondary but entirely wanted effect, as creatine transport through the peritoneum is not passive by simple diffusion, as in hemodialysis, but actively mediated via a specific sodium chloride-dependent creatine transporter (CRT). Thus only a very small fraction of the actual creatine compound, to which the peritoneum is exposed to, is taken up via CRT.

Most importantly this CRT-mediated uptake is governed by the actual physiological needs and requirements of the patient's body for creatine and thus no overloading by creatine compounds is possible by peritoneal dialysis, even though an excess of creatine may be offered in the fluid. This novel strategy to be able to reduce, by addition of high concentrations of creatine compounds, the exposure of the patients to very high glucose levels and at the same time allow for physiological uptake of creatine compound avoids the numerous unwanted potential side-effects eluded to below.

Chang et al., Nephrol. Dial. Transplant, 17: 1978-1981 (2002) teaches that creatine monohydrate treatment alleviates hemodialysis-associated muscle cramps (HAMC), which are assumed to be the result of disturbances in the muscle energy metabolism, intradialytic hypotension, excessive ultrafiltration and/or elevation of serum creatine kinase. For this purpose ten patients with frequent muscle cramps during hemodialysis were selected, five for the creatine supplementation group and five for the placebo group. To the creatine receiving group 12 g creatine monohydrate in 100 ml water were administered orally 5 minutes before starting hemodialysis. The authors claim that there was a 60% decrease in muscle cramps in the creatine receiving group and that serum creatinin increased from 10.7 to 12.4 mg/dl in the four week treatment period.

Next to the limited number of patients in each group (five each) it should be recognized that 12 g of creatine monohydrate are not easily solubilized at once and ingested creatine that has to be taken up by intestinal epithelial cells will take about two to four hours to reach maximal levels in the blood stream. Hence, the timing of the administration of creatine five minutes before starting dialysis is irrelevant for its alleged effect. The authors themselves admit that further long term, large-scale studies are mandatory to confirm the effects and safety of creatine monohydrate supplementation in HAMC because of the small number of patients and brief follow-up period.

US patent application 2003/0013767 A1 teaches a method of using a creatine compound to specifically treat weight loss associated with liver and kidney diseases and in this respect discloses a dialysis fluid for hemodialysis containing 1.5 g creatin/100 ml corresponding to a concentration of 114.4 mM/l. The disadvantage of such high concentrations of creatine for hemodialysis, however, are:
1) During hemodialysis, creatine may precipitate or crystallize in different parts of the hemodialysis machine.
2) Such high concentrations of creatine during hemodialysis are neither necessary nor desired because they are far from physiological and in fact are two orders of magnitudes higher than the concentrations of those serum creatine concentration that are reached post-prandial after a meal rich in fish or meat or after direct oral creatine supplementation with 5-20 g of chemically pure creatine.
3) A chronic overload with creatine is bound to down-regulate endogenous creatine bio-synthesis in the body (Guerrero and Wallimann 1998), whereas moderate creatine supplementation, even if given long-term as proposed herein, is not.
4) A chronic overload of a dialysis patient with creatine is a burden for the liver if its creatine storage is exhausted by excess creatine supply
5) A chronic overload with creatine leads to ATP-depletion, for cellular ATP will be used for phosphorylation of creatine taken up into the target organs to produce phospho-creatine (PCr)
6) Creatine overload has been shown to influence cell signaling, e.g. to activate the low-energy-sensor and cellular stress-responding AMP-activated protein kinase (AMPK), with potentially unknown side-effects, and
7) High oral dosage of creatine have been shown to influence inflammatory markers and hormone responses that may not be desired for dialysis patients In view of the above it is the objective of the present invention to provide new means for alleviating or avoiding disorders and/or side effects directly or indirectly attributed to hemodialysis treatment. Furthermore, it is the objective to provide new medical indications and new medical compositions for creatine supplementation.

The present invention is predicated, at least in part, by the surprising and unexpected discovery that creatine supplementation at very tow concentrations to a hemodialysis solution can alleviate or avoid disorders and/or side effects directly or indirectly attributed to hemodialysis treatment, in particular mechanical, oxidative, pro-apoptotic, metabolic and immunological stress of the blood cells being dialyzed.

In view of this discovery and in a first aspect the present invention provides a new (haemo)dialysis solution comprising one or more creatine compound(s) in a concentration equivalent of 0.002 to 45 mM/l creatine, preferably of 0.05 to 40 mM/l ans most preferably of 0.05 to 20 mW creatine.

The term "concentration equivalent to 0.05 to 20 mM/l creatine" refers to a total concentration of 0.05 to 20 mM/l for all creatine compound(s) in the dialysis solution.

The term dialysis solution as used herein is any solution suitable for the safe treatment of renal failure by dialysis including hemodialysis, peritoneal dialysis, hemofiltration and hemodiafiltration. It is the solution Into which the blood solutes of small and moderate size (typically 15 to 50, preferably 20 to 35, more preferably about 25 kDa) diffuse during dialysis. It typically comprises mineral salts and buffer substance(s) In physiologically acceptable concentrations. Additionally, it may comprise nutrients, e.g. glucose and amino acids, anticoagulants such as heparin, antioxidants and other physiologically or medically relevant compounds. Naturally, its pH and osmolality is physiologically acceptable.

The creatine compound in the dialysis solution may be any physiologically acceptable creatine and/or phosphocreatine ((phospho)creatine) compound, derivative, analog and/or precursor thereof that will eventually raise the creatine and phosphocreatine level to normal physiologically healthy concentrations in the blood of the dialysis patient. For example, suitable creatine compounds and derivatives are (phospho)creatine, (phospho)cyclocreatine, homocyclocreatine, (phospho)creatine monohydrate, (phospho)creatine salts such as creatine -pyruvate, -lactate, -ascorbate, -acetate, -citrate, -hydroxycitrate, -aleurate, -phytate, -mandelate, -malate, -glycolate, -cinnamate, -salicylate, -hyluronate, -$\beta$-hydroxybutyrate, -gluconate, -choline, -camitine, -propionyl camitine, -coenzyme Q10, -adenosine, -fructose, -fructose-1,8-biphosphate, etc. Other examples are the ester of creatine-adenosine, the acid anhydride of creatine-glutamine and the acid anhydride of creatine pyruvate. Preferred creatine ascorbyl derivatives for practicing the present invention are those specifically mentioned in WO 2008/137137 A1 in claims 1 to 11, which are hereby incorporated in their entirety by reference. Further preferred creatine derivatives are those specifically mentioned in WO 2007/133731 A2 in claims 1 to 11, which are hereby incorporated in their entirety by reference, more preferably creatine-ligand compounds, wherein the ligand is selected from the group consisting of an aminoacid, a water-soluble vitamin, preferably vitamin C or a vitamin B complex vitamin, preferably, selected from the group consisting of thiamine, riboflavin, pyridoxine, niacin, vitamin B12, folic acid, pantothenic acid, biotin, resveratrol, omega-fatty acids, poly-unsaturated fatty acids, linoteic acid, S-adenosine-methionine (SAM), L-camitine, and betaine.

Preferred creatine precursors are guanidinoacetic acid, 3-guanidinopropionic acid, guanidino benzoic acid and the combination of the three basic building blocks of creatine glycine, arginine and methionine as well as their physiologically acceptable salts and derivatives. For precursors, it is noted that one or more precursors may be necessary to form one creatine compound. Hence, for precursors the term "in a concentration equivalent to 0.05 to 20 mW creatine" should be interpreted as the amount of precursors necessary for providing to 0.05 to 20 mM/l creatine.

Creatine analogs are compounds lacking creatine structure but mimicking its biological activity in vivo. Preferred creatine analogs are those specifically mentioned in EP 1 719 510 A1 in claim 2 and in claim 7 of US 2009/0005450 A1, which are hereby incorporated in their entirety by reference.

Typically, healthy humans have a fasting concentration of creatine compounds in the serum of about 20 to 40 µM/l. Upon consumption of creatine-containing food, like fish and meat, this concentration transiently increases to 1 to 2 mM/l. Erythrocytes (red blood cells) and immune cells in the blood are able to accumulate creatine inside the cell via the creatine-transporter (CRT) and due to the presence of creatine kinase (CK) in these cells, some of the creatine is converted to phospho-creatine, such that these cells contain approximately ⅔ of phospho-creatine and ⅓ of creatine. The concentration of total creatine (phospho-creatine plus creatine) in erythrocytes is approximately 0.5 to 1 mM/l, depending on the cell age, and in white blood cells approximately 0.75 to 1.25 mM/l.

Whereas creatine concentrations as high as feasible (solubility limitation) are good for muscle mass maintenance, as taught in the prior art, the concentration of creatine compound(s) of the hemodialysis solution of the invention may be much lower than the (phospho)creatine concentration in the blood of a healthy human and still be physiologically highly effective in protecting dialysed blood cells. This effect is due to the active uptake of creatine and most creatine compound(s) by blood cells. As mentioned before, under physiological conditions blood cells comprise (phospho)creatine in a concentration about 10-50 times higher than the concentration In the surrounding serum. Hence, creatine compounds in the dialysis solution of the present invention will be actively taken up by cells and thus accumulate in blood cells providing the desired cell protective and anti-apoptotic effects.

Therefore, in a preferred embodiment, the dialysis solution of the invention comprises one or more creatine compound(s) in a concentration equivalent to 0.05 to 20 mM/l creatine, 0.05 to 15 mM/l, 0.05 to 10 mM/l, preferably 0.1 to 10 mM/l, most preferably 0.1 to 5 mM/l, also preferably 0.1 to 2.0 or 0.1 to 1.0 mM/l creatine. Additionally, it is noted that the concentration range of creatine compounds in the dialysis solution of the present invention may have a lower value selected from 0.001, 0,002, 0.003, 0.004, 0.005, 0.01, 0.02, 0.03, 0.04, 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.5, 2, 2.5, 3, 3.5, 4, 4.5, 5 mM/l and an upper value selected from 1, 1.5, 2, 2.5, 3, 3.5, 4, 4.5, 5, 6, 7, 8, 9, 10, 11, 12, 13, 14, 15, 16, 17, 18, 19, 20 mM/l. All of the above lower and upper values may be combined to ranges for concentrations for creatine compounds suitable for a dialysis solution of the invention and all of the options resulting therefrom are considered as being specifically listed and fully disclosed.

Depending on the type and mode of dialysis, the extent of renal dysfunction and other physiological parameters, a patient typically receives a volume of a dialysis solution in the range of 5 to 200 liters, regularly about 100 to 600 liters per treatment session, typically 120 to 170 l within a time period of about 3 to 8 hours. Depending on treatment duration and bloodflow (100 to 400 ml/min) 18 to 192 liters blood is regularly presented to the dialysis solution.

The skilled person is fully enabled and aware of how to prepare, adjust, sterilize, store and utilize common dialysis solutions. The principles of hemodialysis and the basic requirements for preparing dialysis solutions have been known since the late 1940s. For a more detailed discussion of hemodialysis and hemofiltration reference is again made to Kuhlmann, Walb, Luft, Nephrologie, $4^{th}$ ed., chapter 15, 516, 2003 et seq. and to the sales brochure "Hämodialyse; Konzentrate and Lösungen für die Dialyse", Lieferprogramm, Fresenius Medical Care, 2008, both of which are hereby incorporated by reference.

A common dialysis solution typically comprises the mineral ions Na—, K—, Ca—, Mg—, Cl— and at least one buffering substance adjusting and buffering the pH to a physiologically acceptable value, most commonly in the range of 7 to 7.8, preferably to 7.1 to 7.5, more preferably to 7.2 to 7.4.

Because dialysis reduces the carbohydrate-based energy content of the dialyzed blood and thereby depletes the patient of energy, most dialysis solutions comprise glucose and/or some other carbohydrate source of energy. However, in the case of the dialysis solution of the present invention, the creatine compound(s), in particular the phosphorcreatine compound(s) can supplement for the lost energy. On the other hand, it is probably still beneficial to have some carbohydrate energy source in the dialysis solution of the present invention in order not to unbalance the glycolysis hemostasis in the cells. Moreover, creatine compounds have been shown to elicit pharmaceutically beneficial effects when given in combination with dextrose (glucose) (see e.g. WO 2007/133673 A2). Last but not least, carbohydrate energy sources like glucose In the dialysis solution of the present invention have the advantage that they enable blood cells to energize, i.e. phosphorylate the creatine compounds.

In a preferred embodiment the dialysis solution of the invention further comprises:
(i) Na—, K—, Ca—, Mg—, Cl-ions,
(ii) at least one physiologically acceptable buffering substance, preferably selected from bicarbonate, lactate and/or acetate, and
(iii) optionally but preferably a carbohydrate source, more preferably glucose, all of (i) to (iii) in physiologically acceptable concentrations.

In an additional preferred embodiment the dialysis solution of the present invention may also comprise any physiologically acceptable additive in physiologically acceptable concentrations, preferably additives selected from the group consisting of water-soluble vitamins, trace elements, nutrients, preferably amino acids.

As mentioned above creatine compounds suitable for use in this invention are any physiologically acceptable creatine and/or phosphocreatine compounds, derivatives, analogs and/or precursors that will eventually raise the creatine and phosphorcreatine level to normal physiologically healthy concentrations in the blood and body of the dialysis patient.

In a preferred embodiment the creatine compound(s) of the dialysis solution of the present invention is(are) selected from the group consisting of:
(i) (phospho)creatine compounds, preferably (phospho)creatine, (phospho)creatine monohydrate, (phospho)cyclocreatine, homocyclocreatine,
(II) (phospho)creatine derivatives, preferably (phospho)creatine salts, more preferably creatine -pyruvate, -lactate, -ascorbate, -acetate, -citrate, -hydroxycitrate, -aleurate, -phytate, -mandelate, -malate, -glycolate, -cinnamate, -salicylate, -hyaluronate, -β-hydroxybutyrate, -gluconate, -choline, -camitine, -propionylcarnitine, -coenzyme Q10, -adenosine, -fructose, -fructose-1,6-biphosphate, esters of creatine-adenosine, acid anhydrides of creatine-glutamine and creatine pyruvate,
(iii) creatine precursors, preferably guanidinoacetic acid, 3-guanidinopropionic acid, guanidino benzoic acid and the combination of glycine, arginine and methionine as well as their physiologically acceptable salts and derivatives, and
(iv) creatine analogs, preferably those disclosed above by specific reference.

In a more preferred embodiment, the creatine compound(s) of the dialysis solution of the present invention is(are) selected from the group consisting of (phospho)creatine compounds, preferably (phospho)creatine, (phospho)creatine monohydrate, and (phospho)creatine salts, preferably pyruvate, lactate, ascorbate, acetate, citrate and hydroxycitrate.

Most of the creatine compounds will contribute to the osmolality of the dialysis solution of the invention. It goes without saying that the osmolality of the dialysis solution of the invention must be adjusted to meet physiologically acceptable limits. Because the concentration of the creatine compounds in the dialysis solution of the present invention is very low, much lower than recommended for anti-catabolic effects, these creatine concentrations will not cause any osmolaltity problems.

In a specific non-limiting and preferred embodiment, the dialysis solution of the present invention, essentially consists of:
a) 0.05 to 20, preferably 0.1 to 10, more preferably 0.5 to 10, most preferably 0.1 to 5 mmol/l creatine compound(s), b) 130 to 150, preferably 135 to 145, more preferably about 138 mmol/l Na ions,
c) 0 to 10, preferably 1 to 6, more preferably 1 to 4 mmol/K ions,
d) 0,5 to 3, preferably 1 to 2, more preferably 1 to 1.25 mmol/Ca ions,
e) 0 to 10, preferably 1 to 6, more preferably 1 to 4 mmol/Mg ions,
f) 0 to 10, preferably 1 to 6, more preferably 1 to 4 mmol/Cl ions, and preferably comprising
g) 0.2 to 3 g/l, preferably 0.5 to 2.5 g, more preferably 1 to 2 g/l glucose, as well as
h) 25 to 40, preferably 28 to 35, more preferably about 32 mmol/l bicarbonate ions, and
i) 1 to 5, preferably 2 to 4, more preferably 2 to 3 mmol/l acetate ions, as physiologically acceptable buffer substances, and
j) optionally further physiologically acceptable compounds in physiologally acceptable concentrations wherein the theoretical osmolality of the dialysis solution is 270 to 310, preferably 280 to 305, more preferably 285 to 300, most preferably 287 to 298 and the pH is in the range of 7.1 to 7.5, preferably 7.2 to 7.4.

Because large amounts of dialysis solutions are typically required for hospital dialyzers, it is common in the art to produce dry and aqueous concentrates for preparing dialysis solutions that are manually or automatically diluted, admixed (multiple component systems), sterilized and warmed to body temperature. In the case of less soluble components, in particular minerals such as magnesium and calcium, the about pH-neutral ready-to-use dialysis solutions are often produced and stored as acidic and/or basic solutions and/or concentrates. In particular bicarbonate-buffered dialysis solutions tend to precipitate carbonates at neutral to basic pH if stored over prolonged times. Therefore, the bicarbonate component is typically added to the dialysis solution of the dialyser only shortly before the administration of the dialysis solution to the patient. Standard commercial concentrates for dialysis solutions are multiple (mostly two) part systems, usually comprising (i) a dry or aqueous bicarbonate concentrate in a container such as a bag or cartridge and (ii) a dry or aqueous mineral concentrate in a container such as a canister optionally comprising further non-mineral components such as glucose.

The term "dialysis solution" as used herein is meant to indicate any ready-to-use dialysis solution or component of a dialysis solution that does not require further dilution before administering it to a patient in need thereof. The term "dialysis concentrate" as used herein is meant to indicate any dry or aqueous dialysis solution component that requires at least aqueous dilution and optionally addition of further components before becoming a ready-to-use dialysis solution suitable for administering to a patient in need thereof, According to the present invention the creatine compound(s) can be present in (i) a ready-to-use dialysis solution, but also in (ii) a dry or aqueous concentrate as a one component dialysis system or (iii) a dry or aqueous concentrate being part of a multi-component dialysis system for preparing a ready-to-use dialysis solution.

In another aspect the present invention is directed to a dry or aqueous dialysis concentrate comprising (i) at least one creatine compound and (II) physiologically acceptable ions and/or at least one buffering substance(s), wherein said concentrate results in a dialysis solution according to the invention upon aqueous dilution and optionally addition of further substances.

(Phospho)creatine and many of the creatine compounds for use in the present invention have a tendency to form creatinine at an acidic pH and higher temperatures by a spontaneous non-enzymatic reaction. Hence, it is of advantage to avoid creatinine formation by keeping creatine compounds in dialysis solutions and dry or aqueous concentrates of the invention at low temperatures and a neutral to basic pH. If kept as aqueous solution, it is preferably cooled to 2 to 5° C., because the chemical stability of creatine is enhanced and storage life of the solution is extended in the cold. However, even under neutral and alkaline conditions, e.g. pH 7.0 to pH 8.5, dialysis solutions and concentrates of the invention can comprise creatine compounds without significant creatinine formation for an acceptable time span that can be extended by storage in the cold.

Hence, in a preferred embodiment the present invention also relates to an acidic dialysis concentrate, comprising
(i) Na—, K—, Ca—, Mg— and Cl-ions,
(ii) at least one creatine compound,
(iii) optionally at least one physiologically acceptable buffering substance, preferably selected from bicarbonate, lactate and/or acetate
(iv) glucose,
in concentrations providing for physiologically acceptable concentrations and a pH in the range of 7.1 to 7.5 upon dilution and addition of at least one basic physiologically acceptable buffering substance, preferably selected from bicarbonate, lactate and/or acetate.

For example, acidic dialysis concentrates according to the invention can be prepared by adding creatine compound(s) in physiologically acceptable amounts to suitable concentrates.

The osmolality and pH of the acidic concentrate has to be adjusted depending on the type and amount of creatine compound(s) added.

Because of better stability a more preferred embodiment of the invention is directed to a basic dialysis concentrate comprising at least one creatine compound and at least one basic physiologically acceptable buffering substance, preferably selected from bicarbonate, lactate and/or acetate, preferably essentially free of magnesium and calcium. Most preferably, the basic dialysis concentrate of the invention is a bicarbonate concentrate. Dry concentrates have the advantage of avoiding the weight as well as the chemical and biological disadvantages attributed to water, e.g. instability of some components in aqueous environments, oxidation and microorganism growth.

In a most preferred embodiment the present invention relates to a dry dialysis concentrate of the invention, essentially free of water, preferably consisting of at least one creatine compound and at least one basic buffering substance, preferably selected from the group consisting of bicarbonate, lactate and/or acetate.

Preferably a dialysis concentrate of the invention is one for which water dilution by a factor of 25 to 60, preferably 30 to 50, more preferably 32 to 48, most preferably 35 to 45 by weight is required in order to produce a dialysis solution of the invention as described above.

In a further aspect the present invention is directed to the use of at least one creatine compound for preparing a dialysis solution or a dialysis concentrate of the invention. For said use creatine compound(s) as mentioned above are suitable, preferably creatine compound(s) selected from the group consisting of (phospho)creatine compounds, preferably (phospho)creatine, (phospho)creatine monohydrate, and (phospho)creatine salts, preferably pyruvate, lactate, ascorbate, acetate, citrate and hydroxycitrate.

In an additional aspect the present invention pertains to a method for preparing a dialysis solution or a dialysis concentrate of the invention, comprising the steps of admixing at least one (i) creatine compound and (IIe) physiologically acceptable ions and/or (iib) at least one physiologically acceptable buffering substance.

Preferably, the invention relates to the above method resulting in (i) a concentrate useful for preparing a dialysis solution or (ii) a dialysis solution, said dialysis solution essentially consisting of:
a) 0.05 to 20, preferably 0.1 to 10, more preferably 0.5 to 10, most preferably 0.1 to 5 mmol/l creatine compound(s)
b) 130 to 150, preferably 135 to 145, more preferably about 138 mmol/l Na ions,
c) 0 to 10, preferably 1 to 6, more preferably 1 to 4 mmol/K ions,
d) 0.5 to 3, preferably 1 to 2, more preferably 1 to 1.25 mmol/Ca ions,
e) 0 to 10, preferably 1 to 6, more preferably 1 to 4 mmol/Mg ions,
f) 0 to 10, preferably 1 to 6, more preferably 1 to 4 mmol/Cl ions, and preferably comprising
g) 0.2 to 3 g/l, preferably 0.5 to 2.5 g, more preferably 1 to 2 g/l glucose, as well as
h) 25 to 40, preferably 28 to 35, more preferably about 32 mmol/l bicarbonate ions, and
i) 1 to 5, preferably 2 to 4, more preferably 2 to 3 mmol/l acetate ions, as physiologically acceptable buffer substances, and
j) optionally further physiologically acceptable compounds in physiologically acceptable concentrations,
wherein the theoretical osmolality of the dialysis solution is 270 to 310, preferably 280 to 305, more preferably 285 to 300, most preferably 287 to 298 and the pH is in the range of 7.1 to 7.5, preferably 7.2 to 7.4.

In a special embodiment a dialysis solution comprising one or more creatine compound(s) in a concentration equivalent to 0.002 mM/l to 45 mM/l, preferably to 0.05 mM/l to 40 mM/l at 37° C. is used for hemodialysis.

Other embodiments a dialysis solution comprising one or more creatine compound(s) in a concentration equivalent to 40 mM/l to 200 mM/l 37° C. is directed to the use for peritoneal dialysis, wherein the creatine compounds are acting as osmolyte. Preferably the the concentration is equivalent to 115 mM/l to 200 mM/l at 37° C., most preferably to 120 mM/l to 200 mM/l at 37° C.

A further embodiment is directed to the use of an unsaturated dialysis solution comprising one or more creatine compound(s) for peritoneal dialysis, wherein the creatine compounds are acting as osmolyte. Said dialysis solution can further comprise one or more organic osmolytes from the following three classes of compounds:
A) polyols, preferably inositol, myo-inositol or sorbitol;
B) methylamines, preferably choline, betaine, carnitine (L-, D- and DL forms), n-acetyl-carnitine, L-carnitine derivatives, phosphorylcholine, lyso-phosphorylcholine or glycerophosphorylcholine; and
C) amino acids.

A further embodiment is directed to a dialysis solution comprising one or more creatine compound(s) in a concentration equivalent to 40 to 200 mM/l creatine and an amount of glucose inferior to 106 g/l, preferably inferior to 62.6 g/l and most preferably inferior to 37.5 g/l.

Last but not least, one more aspect of the present invention is directed to a method of treatment comprising the step of administering a dialysis solution according to the Invention in a physiologically effective volume to a patient in need thereof, e.g. for blood detoxification. A further aspect of this invention is directed to a method for treating a patient with renal dysfunction, said method comprising
a) in a first step the oral administration of a creatine compound; and
b) in a second step the dialysis with a creatine compound.

By "treating" is meant the slowing, interrupting, arresting or stopping of the progression as well as the preventing of the onset of a disease or condition associated with renal dysfunction and/or dialysis treatment and treating does not necessarily require the complete elimination of all disease symptoms and signs. "Preventing" is intended to include the prophylaxis of a disease or condition, wherein "prophylaxis" is understood to be any degree of inhibition of the time of onset or severity of signs or symptoms of the disease or condition, including, but not limited to, the complete prevention of the disease or condition.

This and other objects of the present invention as well as additional inventive features, will be apparent from the detailed description provided herein.

Unless otherwise defined, all technical and scientific terms used herein have the same meaning as commonly understood by one of ordinary skill in the art to which this invention pertains.

Preferred methods and materials are described below, although methods and materials similar or equivalent to those described herein can be used in the practice or testing of the present invention. The following example serves to illustrate further the present invention and is not intended to limits its scope in any way.

EXAMPLE 1

For a clinical set-up 0.1 to 30 g of creatine (m.w. 131.13 g/mol) can be added to a dialysis concentrate of about 4.7 liters (that is normally used for one dialysis treatment per patient per day in a dialysis machine) to provide a final concentration of creatine compound(s) of 0.16 to 48 mM/l in the concentrated dialysis fluid or stock solution. For creatine the concentration of 6.4 g per liter dialysis concentrate corresponds to the maximum solubility of creatine in water at neutral pH at a temperature of about 5 degree Celsius. A higher concentration for creatine is not feasible if the dialysis concentrate is to be cooled for stability purposes without the risk of precipitation.

With a typical dialysis flux rate of 800 ml/min over a period of 4 h—amounting to a dilution of the above concentrated dialysis fluid during the dialysis process to a final volume of 192 liters of actual dialysis fluid (corresponding to a dilution factor of the dialysis stock solution of about 40 fold)—the effective creatine concentrations in the final dialysis solution will be 0.004 to 1.2 mM/l.

Because the creatine transporter protein (CrT) in the plasma membrane has a very high affinity to creatine with a km of approximately 25 to 30 micromolar, the mentioned concentrations of creatine in the final dialysis solution (0.004-1.2 mM/l) are in the range of or significantly above the km of the creatine transporter, allowing for the efficient uptake of creatine compounds by blood cells from the final dialysis solution.

Typically, 20 to 30 g of creatine added to 4.7 liters of dialysis concentrate are used to give a creatine concentration of 32 mM-48 mM/l stock concentration, getting diluted in the final dialysis solution of 0.8 to 1.2 mM/l. Because the patient's blood is continuously in contact with these concentrations of creatine during the entire treatment, and because the CrT is efficient in transporting creatine into the cells, the cells are loaded with creatine.

The above-mentioned concentrations of creatine in the final dialysis solution of about 1 mM are considerably lower than those proposed by prior art documents teaching creatine supplementation for dialysis patients for maintaining and building muscle mass, but are highly effective for cell protection. During the dialysis process using the inventive dialysis solution with very low creatine concentrations the patient is eventually exposed to all of the creatine that was originally added to the concentrated dialysis fluid. The resulting creatine concentrations are physiological, e.g. such concentrations of creatine occur post-prandially in the serum of a human after a good meal of meat of fish. The creatine concentrations in the dialysis solution do not elicit any side effects and will not lead to undesired and unhealthy down-regulation of endogenous creatine synthesis in the patient.

EXAMPLE 2

As a preferred practical example for direct oral Creatine supplementation of dialysis, patients would orally ingest Creatine, Cr-monohydrate or other Cr-containing compounds, e.g. Cr-salts or Cr-analogs. These Creatine-containing compounds would be taken orally in form of a powder or tablets, or as an aqueous solution or suspension. The preferred supplementation scheme allows for 1-20 g of Creatine or Creatine compounds per day for a loading phase period of 7-14 days, followed by a maintenance phase of 2-5 g of Creatine per day during unlimited time or as long as needed.

Additionally to this oral supplementation creatine was given to the patient also by dialysis at a concentration of 2 mM/l.

EXAMPLE 3

As a preferred practical example for a clinical haemodialysis setting, 1-30 g of Creatine are added to the haemodialysis concentrate of 5 liters (normally used for one haemodialysis treatment per patient per day, in a commercial haemodialysis machine) to give a final creatine concentration of 0.08-45 mM/l in the dialysis concentrate.

With a typical dialysis flux rate of 800 ml/min over a period of 4 hrs, amounting to a dilution of the above concentrated dialysis fluid during the dialysis process to a final volume of 190 liters of actual dialysis fluid (corresponding to a dilution factor of the dialysis concentrate of approximately 40 fold), the effective creatine concentrations In the final dialysis solution administered to the patient will be between 0.002-1.125 mM/l.

Since the Creatine Transporter Protein (CrT) in the plasma membrane has a very high affinity to creatine with a km of approximately 25-30 micro molar (Straumann at al. 2006), the latter concentrations of creatine in the final dialysis liquid (0.004-1.125 mM/l) are entirely in the range of or significantly above the km of the Creatine transporter, such that efficient uptake of creatine by the cells from the final dialysis liquid is entirely guaranteed.

Typically, 20-30 g of creatine added to 5 liters of dialysis concentrate are used to give a creatine concentration of 30 mM/l-45 mW. This then gets diluted in the final dialysis fluid to 0.75-1.125 mM/l. Since the patient's blood continuously sees these concentrations of creatine during the entire treatment, and since the CrT is efficient in transporting creatine into the cells, the cells have the chance of fully loading up with creatine during the 3-4 hrs of each dialysis session. Thus, the range of creatine concentration in the final dialysis fluid as proposed herein corresponds to physiological post-prandial creatine concentrations that are reached by oral ingestion of a single dose of 5-20 g of creatine directly or alternatively by consuming a meal rich in fresh fish and meat. Uptake of creatine from the dialysis liquid during the time of haemodialysis of 3-4 hrs is sufficient to allow for optimal uptake of creatine into the body, loading of the target organs and cells with creatine and attaining the beneficial physiological effects, including cell protection, of creatine for the patients, as stated above. Such creatine concentrations, as proposed herein, do not have any side effects and will not lead to any down-regulation of endogenous creatine synthesis In the body.

The concentration of creatine in the final haemodialysis liquid of approximately 1 mM (see above) as proposed here is significantly lower compared to that proposed by patent application US 2003/0013767 A1 by Bessman, but are nevertheless still fully sufficient to allow for the reported cell protection effects described above. In our case, the patient is exposed to the total amount of Creatine that has been added to the concentrated dialysis fluid (1-30 g) during the entire dialysis process, After dilution (see above), those concentrations of creatine are absolutely physiological (approximately 1-2 mM/l), e.g. such a concentration of creatine appears post-prandial in the serum of a human after a good meal of meat or fish or after a single dose of creatine supplementation with 5-20 g of Creatine orally. The values in Bessman's patent application US 2003/0013767 A1 (15 g of Creatine per liter of final dialysis fluid are much higher compared to those proposed herein of 20-30 g creatine diluted in approximately 200 liters of final dialysis fluid equal 0.1-0.15 g of creatine per liter). The concentrations of creatine known in prior art are highly non-physiological for a hemodialysis fluid and likely to exert a high-osmotic pressure and metabolic stress on cells. In addition, as an unfavorable and undesired side effect, exposure of the organism to such very high concentrations of creatine may reduce endogenous creatine synthesis in the body, lower cellular ATP-levels for production of phosphocreatine and activate AMPK, influence hormonal and inflammatory parameters in the body of dialysis patients This is definitely not the case at the lower creatine concentrations proposed here to be used for haemodialysis. Finally, the high concentrations of creatine proposed in the application US 2003/0013767 A1 by Bessman are technically impractical, due to the rather low solubility of creatine in water and the very large temperature-dependence of the creatine solubility. It is a high risk that under the high-concentration conditions proposed by the Bessman patent application US 2003/0013767 A1 of 15 g of Creatine per liter of fluid, which is at the solubility limit of a creatine solution at 25° C., creatine will precipitate in the dialysis fluid with all of the very unfavorable consequences for the practicability of the dialysis process.

EXAMPLE 4

As a preferred practical example for a chronic ambulatory peritoneal dialysis (CAPD) or an automated peritoneal dialysis (APD) setting, 20-24 g of creatine is added per liter of peritoneal dialysis liquid at 37° C., corresponding to a concentration of 150-190 mM/l of creatine. These concentrations of creatine are still below the critical solubility limits at the respective temperatures and thus pose no problem for precipitation. At the same time, these creatine concentrations are high enough to be accounted for as osmotically relevant. Therefore, the glucose concentration in standard peritoneal dialysis fluid can be lowered accordingly. By using other creatine compounds, e.g. creatine salts and analogs that are better soluble in water, the concentration of creatine compounds may be set even higher, and thus more glucose can be replaced, accordingly.

Typically, and preferably 20-24 g of creatine are added per liter of final peritoneal dialysis liquid at 37° C. leading to a final creatine concentration of 150-190 mM/l_37° C. Using this strategy, the amount of glucose in peritoneal dialysis solution of differing strength, e.g. containing 37.5 g/l, 62.6 g/l or 106 g/l, can be reduced by addition of the above 24 g of creatine/l to 13.5 g/l, 38.6 g/l or 82 g/l, respectively. This significantly reduces the glucose load on the peritoneum with its potential negative consequences, as stated above. In fact, since in APD and CAPD the actual 2-3 liters of peritoneal dialysis fluid are exchanged 4-5 times during a single dialysis session, the total glucose sparing effect, that is, the lower exposure of the patients peritoneum to high glucose is 4-5 times higher in absolute terms, e.g. 5×24 g or 120 g of glucose, can be substituted by creatine in one single dialysis session.

Alternatively, for peritoneal dialysis, if high-glucose poses no problem, a total amount of creatine between 5 to maximal 20 g is added directly to the final dialysis liquid, thus representing a similar creatine exposure reached by standard oral creatine supplementation.

The invention claimed is:

1. A hemodialysis or peritoneal dialysis solution comprising one or more compounds selected from the group consisting of:
   (i) creatine;
   (ii) (phospho)creatine;
   (iii) (phospho)cyclocreatine;
   (iv) homocyclocreatine;
   (v) (phospho)creatine monohydrate;
   (vi) guanidinoacetic acid;
   (vii) 3-guanidinopropionic acid;
   (viii) guanidino benzoic acid;
   (ix) a combination of glycine, arginine and methionine; and
   (x) a physiologically acceptable salt of any of (i) through (ix);
   wherein said one or more compounds are present in the hemodialysis or peritoneal dialysis solution at a concentration equivalent to from 0.002 to 45 mM creatine,
   wherein the hemodialysis or peritoneal dialysis solution further comprises physiologically acceptable concentrations of sodium and chloride ions, and at least one physiologically acceptable buffering substance, and
   wherein the hemodialysis or peritoneal dialysis solution does not contain concentrations of any substances that would make the hemodialysis or peritoneal dialysis solution physiologically unacceptable.

2. The hemodialysis or peritoneal dialysis solution of claim 1, wherein said concentration equivalent is from 0.05 to 20 mM creatine.

3. The hemodialysis or peritoneal dialysis solution of claim 2, wherein said concentration equivalent is from 0.05 to 10 mM creatine.

4. The hemodialysis or peritoneal dialysis solution of claim 3, wherein said concentration equivalent is from 0.1 to 5 mM creatine.

5. The hemodialysis or peritoneal dialysis solution of claim 1, further comprising physiologically acceptable concentrations of:
   (i) potassium, calcium and/or magnesium ions, and
   (ii) optionally, a carbohydrate source.

6. The hemodialysis or peritoneal dialysis solution of claim 1, further comprising a physiologically acceptable additive in a physiologically acceptable concentration, wherein said physiologically acceptable additive is selected from the group consisting of water-soluble vitamins, trace elements, nutrients, and amino acids.

7. An aqueous hemodialysis or peritoneal dialysis solution consisting essentially of, in addition to water,
   a) 0.05 to 20 mM of one or more compounds selected from the group consisting of:
      (i) creatine;
      (ii) (phospho)creatine;
      (iii) (phospho)cyclocreatine;
      (iv) homocyclocreatine;
      (v) (phospho)creatine monohydrate;
      (vi) guanidinoacetic acid;
      (vii) 3-guanidinopropionic acid;
      (viii) guanidino benzoic acid;
      (ix) a combination of glycine, arginine and methionine; and
      (x) a physiologically acceptable salt of any of (i) through (ix),
   b) 130 to 150 mM Na ions,
   c) 0 to 10 mM K ions,
   d) 0.5 to 3 mM Ca ions,
   e) 0 to 10 mM Mg ions,
   f) 0 to 10 mM Cl ions,
   g) 0.2 to 3 g/l glucose,
   h) 25 to 40 mM bicarbonate ions, and
   i) 1 to 5 mM acetate ions, as physiologically acceptable buffer substances,
   wherein the theoretical osmolality of the hemodialysis or peritoneal dialysis solution is 270 to 310 and the pH is in the range of 7.1 to 7.5, and
   wherein the hemodialysis or peritoneal dialysis solution does not contain concentrations of any substances that would make the hemodialysis or peritoneal dialysis solution physiologically unacceptable.

8. The hemodialysis or peritoneal dialysis solution according to claim 1, wherein the solution does not contain (phospho)creatine.

9. The hemodialysis or peritoneal dialysis solution of claim 8, wherein said concentration equivalent is from 0.05 to 20 mM creatine.

10. The hemodialysis or peritoneal dialysis solution of claim 8, wherein said concentration equivalent is from 0.05 to 10 mM creatine.

11. The hemodialysis or peritoneal dialysis solution of claim 8, wherein said concentration equivalent is from 0.1 to 5 mM creatine.

12. The hemodialysis or peritoneal dialysis solution of claim 8, further comprising physiologically acceptable concentrations of:
   (i) potassium, calcium and/or magnesium ions, and
   (ii) optionally, a carbohydrate source.

13. The hemodialysis or peritoneal dialysis solution of claim 8, further comprising a physiologically acceptable additive in a physiologically acceptable concentration, wherein said physiologically acceptable additive is selected from the group consisting of water-soluble vitamins, trace elements, nutrients, and amino acids.

* * * * *